(12) United States Patent
Farris et al.

(10) Patent No.: US 7,749,256 B2
(45) Date of Patent: Jul. 6, 2010

(54) RATCHETING FIXATION PLATE

(75) Inventors: Robert A. Farris, Cordova, TN (US); Jason M. May, Memphis, TN (US); Alexander R. Vaccaro, Gladwyne, PA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 859 days.

(21) Appl. No.: 11/099,007

(22) Filed: Apr. 5, 2005

(65) Prior Publication Data

US 2006/0235398 A1  Oct. 19, 2006

(51) Int. Cl.
*A61B 17/80* (2006.01)
(52) U.S. Cl. ...................................... 606/282
(58) Field of Classification Search .............. 606/61, 606/69, 280, 70, 71, 281–299
See application file for complete search history.

(56) References Cited

U.S. PATENT DOCUMENTS

| | | | |
|---|---|---|---|
| 3,604,414 A | 9/1971 | Nicomedes | |
| 3,950,001 A * | 4/1976 | Weigl | 280/618 |
| 4,554,914 A | 11/1985 | Kapp et al. | |
| 5,129,903 A | 7/1992 | Luhr et al. | |
| 5,261,911 A | 11/1993 | Carl | |
| 5,616,142 A | 4/1997 | Yuan et al. | |
| 5,964,763 A | 10/1999 | Incavo et al. | |
| 6,051,007 A | 4/2000 | Hogendijk et al. | |
| 6,302,883 B1 | 10/2001 | Bono | |
| 6,328,738 B1 * | 12/2001 | Suddaby | 606/57 |
| 6,402,756 B1 | 6/2002 | Ralph et al. | |
| 6,533,786 B1 | 3/2003 | Needham et al. | |
| 6,689,134 B2 | 2/2004 | Ralph et al. | |
| 6,872,210 B2 * | 3/2005 | Hearn | 606/69 |
| 6,969,398 B2 * | 11/2005 | Stevens et al. | 606/216 |
| 7,318,825 B2 * | 1/2008 | Butler et al. | 606/71 |
| 2002/0055741 A1 | 5/2002 | Schlapfer et al. | |
| 2002/0188296 A1 | 12/2002 | Michelson | |
| 2003/0114856 A1 | 6/2003 | Nathanson et al. | |
| 2003/0130661 A1 * | 7/2003 | Osman | 606/71 |
| 2004/0019353 A1 | 1/2004 | Fried et al. | |
| 2004/0092939 A1 * | 5/2004 | Freid et al. | 606/79 |
| 2004/0097938 A1 * | 5/2004 | Alleyne | 606/69 |
| 2004/0181226 A1 | 9/2004 | Michelson | |
| 2004/0181229 A1 | 9/2004 | Michelson | |
| 2004/0186476 A1 | 9/2004 | Michelson | |
| 2005/0021032 A1 * | 1/2005 | Koo | 606/69 |
| 2005/0043732 A1 * | 2/2005 | Dalton | 606/61 |
| 2005/0216011 A1 * | 9/2005 | Paul | 606/69 |

* cited by examiner

*Primary Examiner*—Eduardo C Robert
*Assistant Examiner*—Tara R George (57) ABSTRACT

Devices and methods for spinal fixation employ at least first and second plates that are configured to allow progressive sliding advancement of the plate members toward one another and limit movement of the plate members away from one another after installation. A spring member associated with one bone plate may engage toothed section(s) on the other bone plate. The bone plates may each have arms that are spaced from one another and engaged by corresponding arms on the other bone plate. There may be more than two bone plates, with multiple restricted movement regions.

51 Claims, 10 Drawing Sheets

RATCHETING FIXATION PLATE

BACKGROUND

Spinal plates have been developed for stabilization of various portions of the spine after various surgical procedures, particularly spinal fusion procedures. Conventional spinal fixation plates typically take the form of a unitary plate with a pair of bone screw openings at opposing ends. The plate is placed over an excavated bone graft-receiving site in the vertebral column, in which a bone graft is located for fusion to adjacent vertebrae, and secured in place with bone screws. These prior art spinal fixation plates fix the adjacent vertebrae on opposite sides of the bone graft-receiving site a set distance relative to one another.

While the fixation plates discussed above are suitable for some situations, they also pose some difficulty in practice due to their lack of adjustability to a particular patient's needs. In particular, such fixation plates have a predetermined length with a predetermined spacing between the screw holes. As such, when a fixation plate with a different spacing is required for a particular patient, another fixation plate must be made available. As the particular needs of a patient may not be known prior to surgery, this necessarily means that multiple sizes of plates must be kept in ready inventory. In response to this, some forms of variable length fixation plates have been proposed, with varying degrees of success. The variable length devices allow the surgeon to adjust the length of the device during surgery, and then to fix that length via suitable locking mechanisms. However, even with variable length devices, the overall length of the device is fixed during surgery and does not change post-operatively.

It has been recognized that it may be beneficial to subject the bone graft to compression over time as the graft fuses to the vertebrae. Use of the conventional fixed length or variable length spinal plates discussed above generally precludes compression of the bone graft beyond any initial compression achieved during the surgical procedure. As such, there remains a need for additional approaches to spinal fixation, advantageously approaches that allow the bone graft to be progressively compressed between adjacent vertebrae over time.

SUMMARY

The present invention is directed to various embodiments of a bone fixation device and methods of use, typically for spinal fixation. One specific embodiment employs at least first and second bone plate members adapted to be secured to bone portions, such as adjacent vertebrae. The bone plate members are configured to allow progressive sliding advancement of the plate members toward one another and limit movement of the plate members away from one another after installation. For example, a spring member associated with one bone plate members may engage toothed section(s) on the other bone plate member. The spring member may be a generally U-shaped spring member abutting the first and second plate members and distinct therefrom. The bone plate members may each have arms that are spaced from one another and engaged by corresponding arms on the other bone plate member. The arms may engage in a male/female relationship, and the distal portions of the male arms may be substantially enclosed by the corresponding female arms. The centerlines of the arms may be substantially aligned when joined. There may be more than two bone plate members, with multiple restricted movement regions. Various combinations of these aspects may also be employed as is appropriate.

DETAILED DESCRIPTION

One embodiment of the present invention is directed to a bone plate device for fixing vertebrae in the spinal column of a patient. One embodiment the device, generally designated 30 in FIG. 1, includes a male bone plate 40, a female plate 80, and a spring lock member 100. The male bone plate 40, disposed in the inferior position in FIG. 1, includes a generally U-shaped body with two arms 60a, 60b and an intervening base section 42. The base section 42 includes two holes 44 for receiving anchoring bone screws 5, which may advantageously be counter-sunk. In addition, the base section 42 may include a third hole 46 for securing a locking ring or other device (not shown) that acts to retain the bone screws 5 in place once they are fully installed. The base section 42 has top 40T and bottom surfaces 40B, which may be flat or advantageously slightly curved to match the orthodic curve of the installation site, as desired. The arms 60a,60b extend from the base section 42 and may advantageously be disposed symmetrically about a midline of bone plate 40, which advantageously coincides with the longitudinal axis 32 of the overall bone plate device 30. In addition, arms 60a,60b have conceptual centerlines 68a,68b that are spaced from each other a distance $D_{MC}$ and advantageously run generally parallel to longitudinal axis 32. With respect to the longitudinal axis 32, the arms 60a,60b have respective inner surfaces 66 and outer surfaces 67. The inner surfaces 66 include respective sections 70a,70b having a plurality of teeth 72 therein, sometimes referred to herein as the toothed sections 70a,70b. The teeth 72 of the toothed sections 70a,70b advantageously have a non-symmetric profile with a generally flat proximal face 74 disposed generally perpendicular to the longitudinal axis 32 and an outwardly angled distal face 75. As can be seen, these toothed sections 70a,70b may be disposed proximally from the distal end portions of the arms 60a,60b. The arms 60a,60b may have variable thickness, such as being thicker in a portion 62 proximal to the base section 42 and thinner in a section 64 distal from the base section 42, with an optional shoulder 63 formed at the change in thickness. The section of the arms 60a,60b extending from proximate the toothed sections 70a, 70b distally to their tips advantageously has a uniform thickness. The inside surfaces 66 of the arms are advantageously joined by a curved portion 43 of the base section 42 corresponding to the inside center of the overall U-shape.

Figure 1:
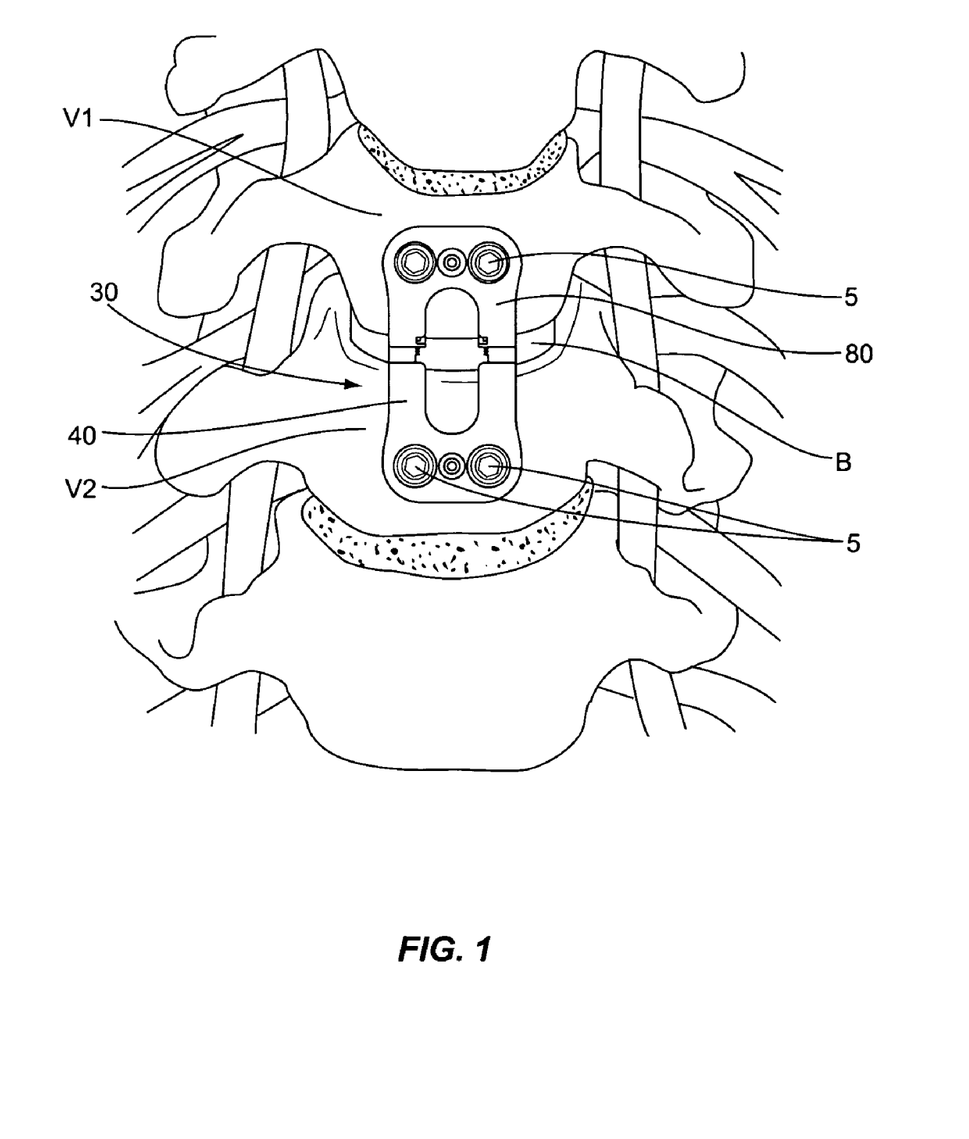
FIG. 1 shows one embodiment of the present invention attached to a cervical portion of a spinal column.
Figure 2:
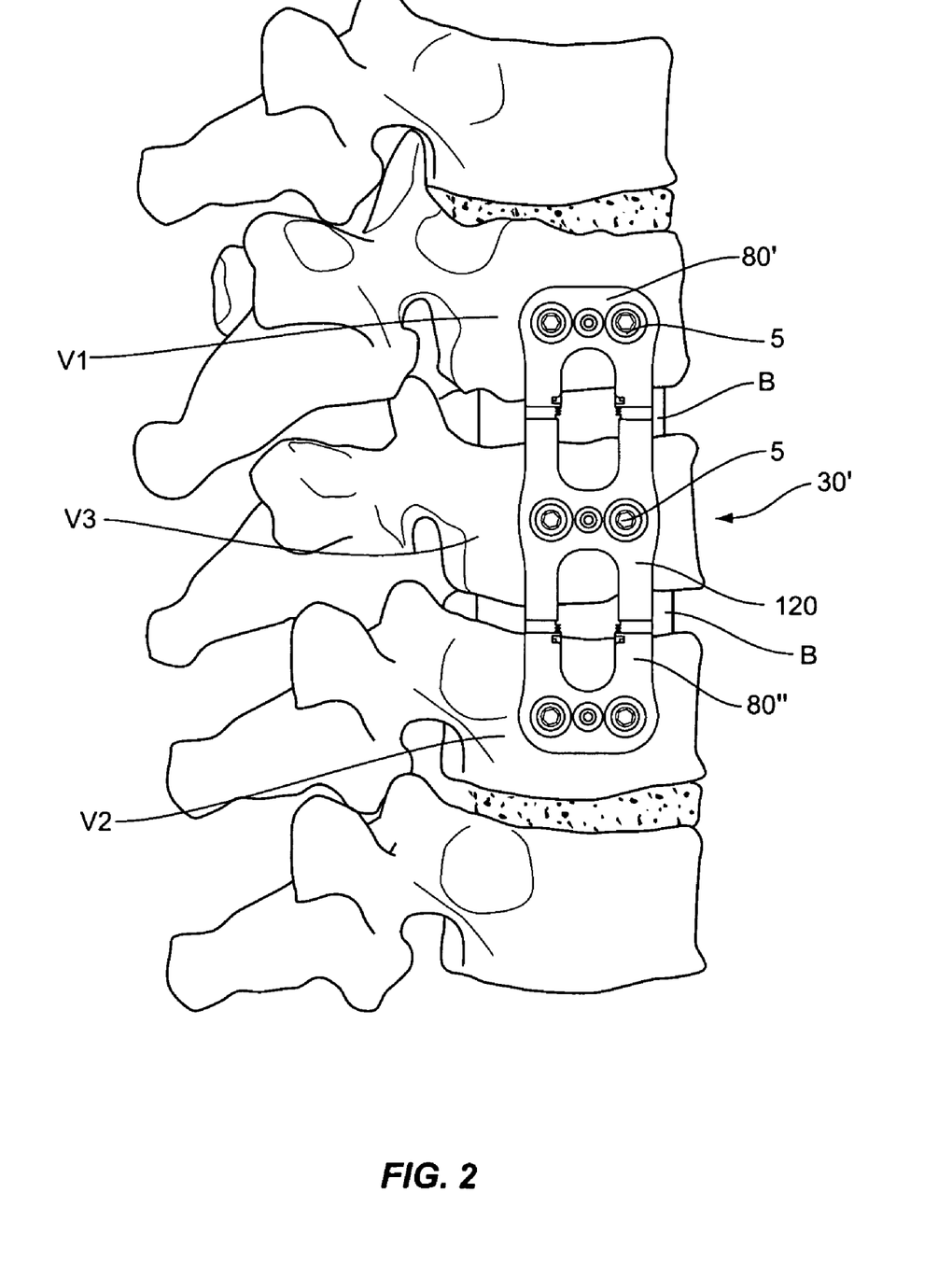
FIG. 2 shows one embodiment of the present invention attached to thoracic and/or lumbar portion of a spinal column.

The female bone plate 80, disposed in a superior position in FIG. 1, includes a generally U-shaped body with two arms 90a,90b and an intervening base section 82. The base section 82 includes two holes 84 for receiving bone screws 5, which may advantageously be counter-sunk. In addition, the base section 82 may include a third hole 86 for securing a locking ring or other device (not shown) that acts to retain the bone screws 5 in place once they are fully installed. The base section 82 has planar top 80T and bottom surfaces 80B, which may be flat or advantageously slightly curved to match the orthodic curve of the installation site, as desired. The arms 90a,90b extend from the base section 82 and may advantageously be disposed symmetrically about a midline of the superior bone plate 80, which advantageously coincides with longitudinal axis 32 of the overall bone plate device 30. In addition, arms 90a,90b have conceptual centerlines 98a,98b that are spaced from each other a distance $D_{FC}$ and advantageously run generally parallel to the longitudinal axis 32. Each arm 90a,90b includes a bay 92 that is intended to receive the distal portion 64 of a corresponding arm 60a,60b of the male bone plate 40, and therefore generally corresponds in cross-sectional shape thereto. With respect to the longitudinal axis 32, the arms 90a,90b have respective inner surfaces $90_{SI}$ and outer surfaces $90_{SO}$. In addition, the arms 90a,90b have respective top surfaces 90T and bottom surfaces 90B, which advantageously continue the shape of top and bottom surfaces 80T,80B of base section 82. A groove 94 may be formed on the inner surfaces $90_{SI}$ that extends along one arm 90a, across the distal curved surface 83 of the base section 82, and along the other arm 90b. Near each end of the groove 94, a small passage 93 connects the groove 94 to the corresponding bay 92. If desired, top surface 90T may include a notch 96 extending outwardly from the longitudinal axis 32 a short distance, proximate the terminal ends of the groove 94. The groove 94 is intended to accept the spring lock member 100, as discussed further below. Advantageously, the arms 90a,90b may have relatively uniform thickness, such as a thickness corresponding to that of the base section 82 of the superior bone plate 80. In addition, it should be noted the inside surfaces $90_{SI}$ of the arms 90a,90b are advantageously spaced a distance apart of $D_{SI}$, which is smaller than distance $D_T$ separating the toothed sections 70a,70b of the inferior bone plate 40.

The spring lock member 100, or simply spring member, is advantageously generally U-shaped, with respective pawl barbs 102a,102b extending outward from the longitudinal axis 32 on each end of the U-shape. The material of the spring member 100 may taper towards the distal portion of the U-shape if desired, for added flexibility. Each pawl barb 102a ,102b, or simply pawl, advantageously has non-symmetric profile with a generally flat proximal face 104 extending generally perpendicular to the longitudinal axis 32, and a sloped distal face 105 that is angled outward and backward to the proximal side of the spring member 100.

The spring member 100 is mated to the female bone plate 80 by inserting the spring member 100 in the groove 94, with the barbs 102a,102b facing outward. The optional notches 96 proximate the terminal portions of the groove 94 aid in seating the barbs 102a,102b properly. It should be noted that the tips of the barbs 102a,102b are intended to extend through the passages 93 and into the corresponding bays 92. The inherent spring force of the spring member 100 helps urge the barbs 102a,102b into position. As such, it may be advantageous for the spring member 100, when in a natural unconstrained state, to have a slightly flatter U-shape, but be required to assume a narrower U-shape by interaction with the superior bone plate 80 (e.g., by being restrained by the groove 94).

With the spring member 100 in place, arms 60a,60b of the male bone plate 40 are inserted into the bays 92 of arms 90a,90b of the female bone plate 80. Advantageously, the two bone plates 40,80 are somewhat loosely coupled at this point, such that they can be moved both toward and away from each other. Such a condition may be achieved, for example, by having the pawls 102a,102b of the spring member 100 bear against the inner surfaces 66 of the arms 60a,60b distally from the toothed sections 70a,70b. For ease of reference, this configuration may be referred to as the pre-installation configuration. The bone plate device 30 may be shipped from the manufacturer in this pre-installation configuration, or the bone plate device 30 may be assembled to this configuration after shipment, but prior to or during surgery.

In use, a surgical site is opened and prepared in any known fashion. At an appropriate point in the procedure, such as shortly after a bone graft implant is placed in position, the bone plate device 30 is installed by securing the bone plates 40,80 to their respective vertebrae V1,V2 using bone screws 5 and holes 44,84. During installation, the length of the bone plate device 30 may be adjusted by sliding the bone plates 40,80 relative to each other. Advantageously, during installation, the bone plates 40,80 are moved toward each other so that pawls 102a,102b of the spring member 100 engage some of the teeth 72 of the toothed sections 70a,70b, such as the distal most teeth 72. For ease of reference, this configuration may be referred to as the partially-engaged configuration. In this partially-engaged configuration, the bone plates 40,80 have limited ability to move apart due to the engagement of the pawls 102a,102b and the toothed sections 70a,70b. However, the bone plates 40,80 may be moved closer together in a progressive ratcheting fashion due to the interaction of the angled faces 75,105 of the pawls 102a,102b and the teeth 72. During this forward or closing movement, the end portions of the spring member 100, proximate the pawls 102a,102b, are deflected inward toward the longitudinal axis 32 until the next tooth 72 is passed, at which point the inherent spring force of the spring member 100 urges the pawls 102a,102b outward to "lock-in" the incremental movement. Thus, the surgeon is able to adjust the bone plate device 30 to the desired initial length prior to closing the surgical site.

Post-operatively, the bone plate device 30 described above is able to continue to shorten (i.e., the proximal portions 48,88 of the bone plates 40,80 are allowed to move toward each other) incrementally, but is limited in its ability to lengthen, thereby helping to ensure proper compression of the bone graft. Of course, as the bone plate device 30 continues to shorten, the bone plates 40,80 will at some point reach a point of maximum movement toward each other. For example, the tips of arms 90a,90b may abut against the shoulders 63 formed on arms 60a,60b where the arms 60a,60b change thickness, thereby preventing further shortening of the bone plate device 30. For ease of reference, this configuration may be referred to as the fully-engaged configuration.

Figure 3:
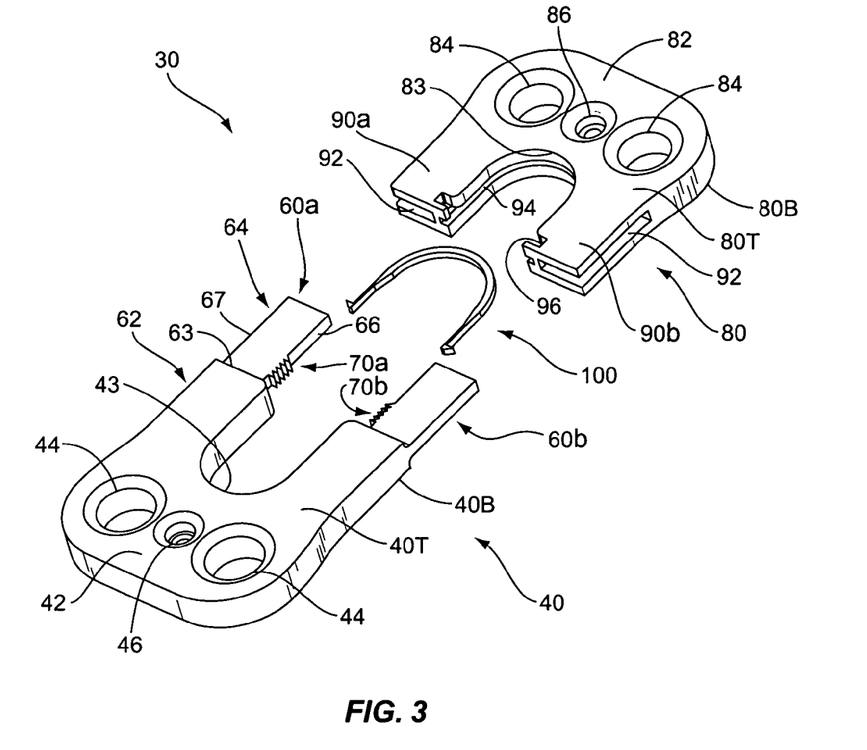
FIG. 3 shows an exploded view of a bone plate device according one embodiment of the present invention.
Figure 4:
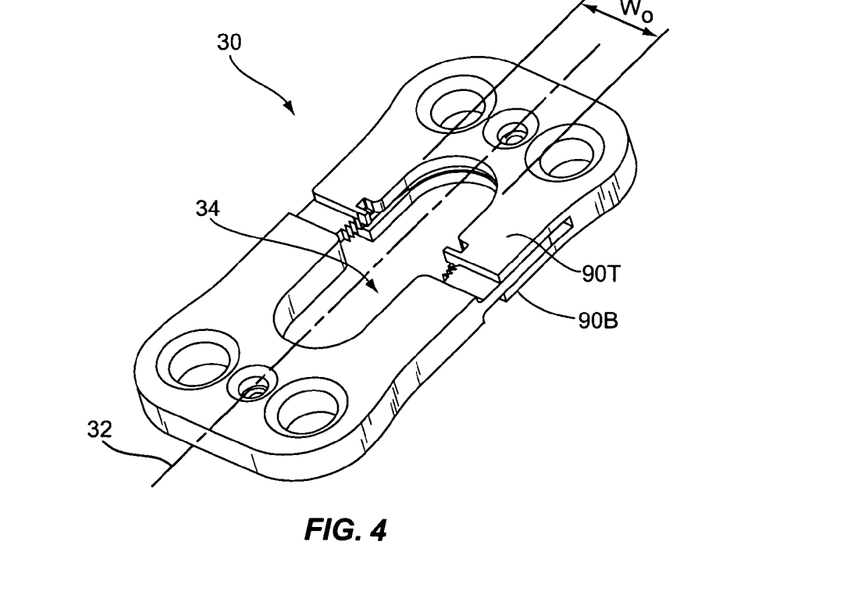
FIG. 4 shows the bone plate device of FIG. 3 in a partially-engaged configuration.
Figure 5:
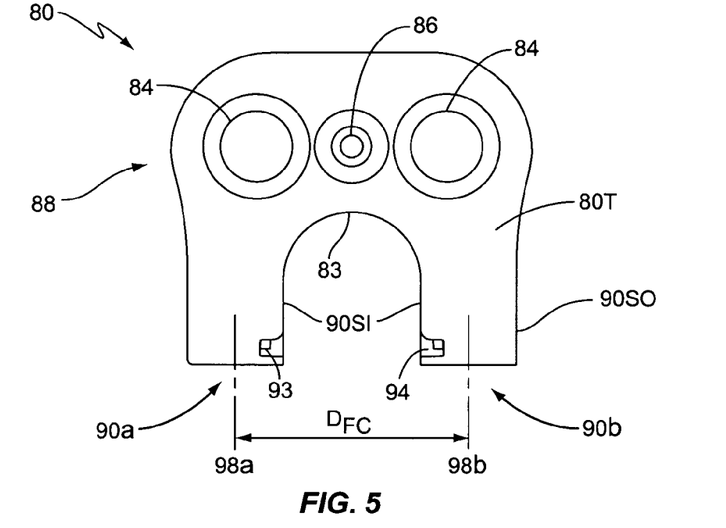
FIG. 5 shows one embodiment of a "female" bone plate portion.
Figure 6:
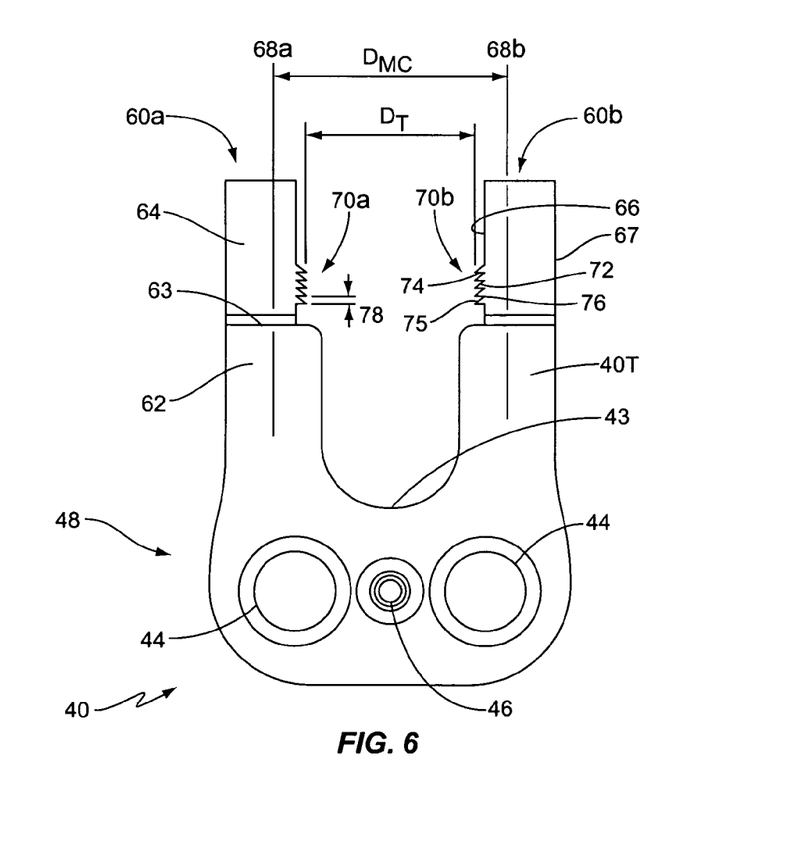
FIG. 6 shows one embodiment of a "male" bone plate portion.
Figure 7:
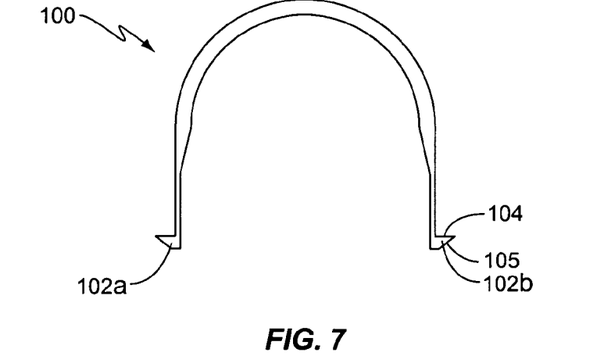
FIG. 7 shows one embodiment of a spring member.
Figure 8:
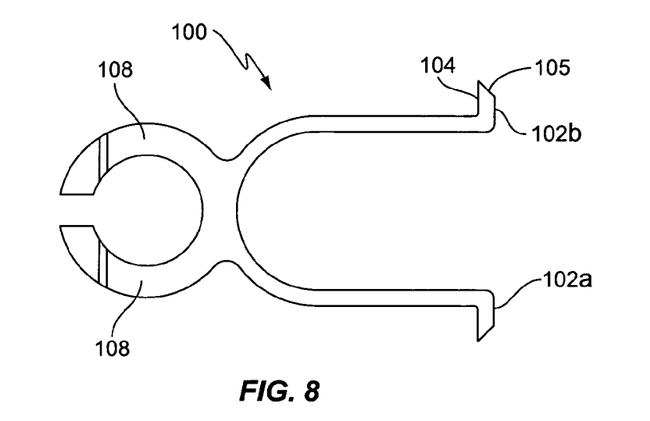
FIG. 8 shows another embodiment of a spring member.
Figure 9:
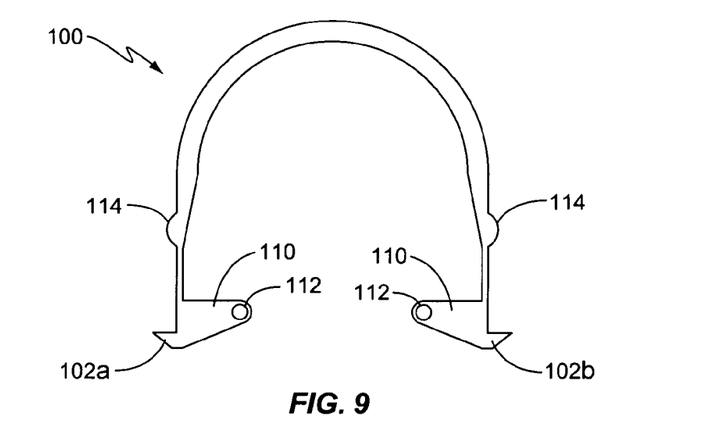
FIG. 9 shows yet another embodiment of a spring member.
Figure 10:
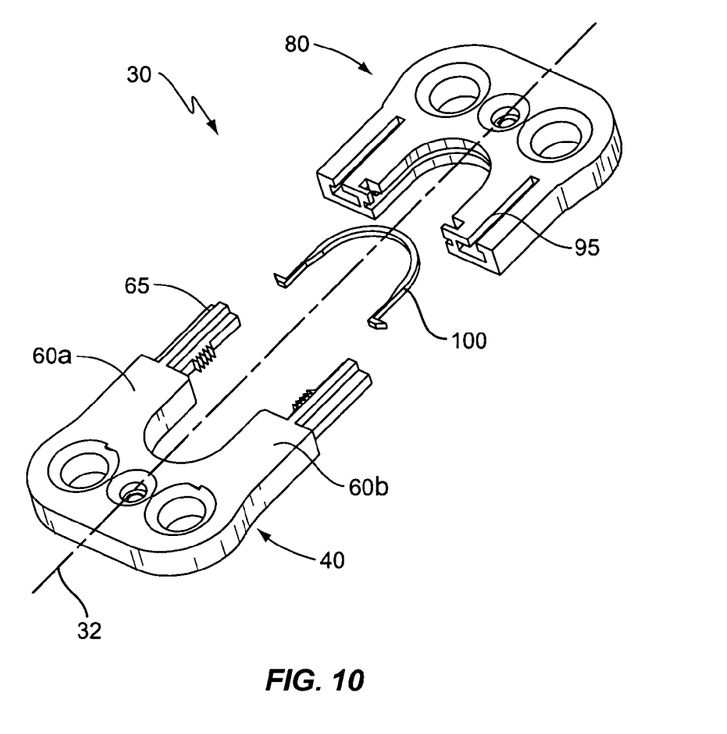
FIG. 10 shows another bone plate device according to another embodiment of the present invention, having guide rails and slots.

As can be seen in FIG. 3, with arms 60a,60b engaging arms 90a,90b, the "female" arms 90a,90b advantageously extend farther inward toward the longitudinal axis 32 than the "male" arms 60a,60b, and also advantageously extend farther outward away from the longitudinal axis 32 than the centerlines 68a,68b of their counterpart arm 60a,60b. In some embodiments, the arms 90a,90b may advantageously extend at least as far outward as their counterpart arm 60a,60b, and optionally farther outward. Indeed, in some embodiments, the female arms 90a,90b may substantially circumferentially enclose the distal portions 64 of the male arms 60a,60b. Further, it should be noted that in some embodiments the distance $D_{FC}$ between the centerlines 98a,98b of arms 90a, 90b is advantageously approximately equal to distance $D_{MC}$ associated with centerlines 68a,68b of arms 60a,60b. While not required in all embodiments, the advantageous spacing and/or general alignment of the arms 60a,60b,90a,90b discussed above allows the curved sections 43,83 of the bone plates 40,80 to help define a generally oval visualization port 34 through the bone plate device 30, thereby allowing the surgeon to easily view the bone graft between the vertebrae V1,V2. Advantageously, this visualization port 34 exists in the pre-installation, partially-engaged, and fully-engaged configurations. The width $W_O$ of the visualization port 34 in a direction generally transverse to a theoretical line connecting the two curved surfaces 43,83, such as along the longitudinal axis 32, is advantageously approximately equal to the distance $D_T$ between the toothed sections 70a,70b in the same direction.

In some embodiments, the spring member 100 may have an additional proximal portion that acts to retain the bone screws 5 in place once they are fully installed. This additional portion may, if desired, take the form of two curved fingers 108 that approximate a split circle. The fingers 108 may sit in a suitable recess in the proximal portion 82 of bone plate 80, and flex inwardly when the bone screws 5 are installed, but spring back out to retain the bone screws 5 with the bone plate 80 and help prevent backing out of the bone screws 5 after they are fully installed. As such, it may be advantageous for the bone screws 5 to include small circumferential shoulders on their heads. Backing out refers to inadvertent removal or significant loosening of the bone screws 5 while installed in the patient; intentional loosening and/or removal of the bone screws 5 by, e.g., a surgeon, is not considered backing out. In other embodiments, the end portions of the spring member 100, proximate the pawls 102a,102b, may optionally include small inwardly extending tabs 110 that may include small holes 112. Pulling inward on such tabs 110, such as with appropriate retaining ring pliers extending through the holes 112, disengages the pawls 102a,102b in the event such is needed to intentionally spread apart the bone plates 40,80. Alternatively, some embodiments allow the pawls 102a,102b to be disengaged by inserting a suitable tool into notches 96 and/or passages 93. In still other embodiments, the legs of the spring member 100 may include small outwardly protruding bumps 114, disposed closer to the base of the U than the pawls 102a,102b, that help retain the spring member 100 with the bone plate 80 by resting in corresponding depressions (not shown) in the arms 90a,90b.

The interconnection between the bone plates 40,80 may, in some embodiments, further include inter-engaging rails 65 and slots 95 that help guide the sliding movement of the bone plates 40,80. In this vein, the distal portion 64 of arms 60a, 60b of bone plate 40 may include rails 65 that extend generally parallel to axis 32, and are advantageously located along centerlines 68a,68b. These rails 65 mate with corresponding slots 95 in the arms 90a,90b of bone plate 80. Alternatively, the rail 65 and slot 95 positions may be reversed.

Figure 11:
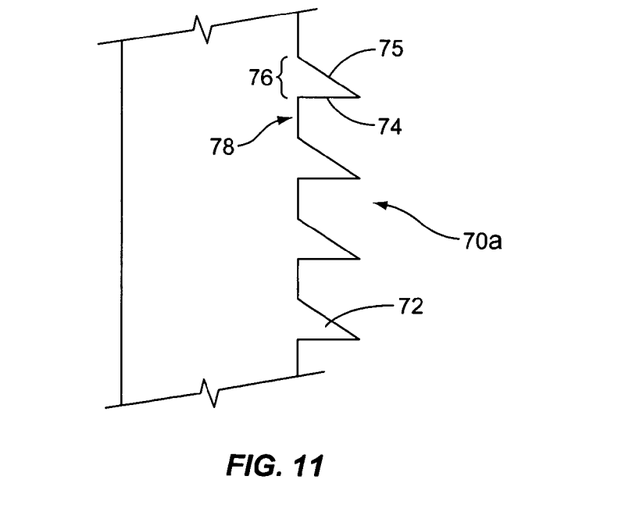
FIG. 11 shows a close up of a toothed section according to one embodiment of the present invention.

The teeth 72 of the toothed sections 70a,70b discussed above have been assumed to be regularly spaced and disposed essentially contiguously, with the base 76 of one tooth 72 abutting the base 76 of the adjacent tooth 72. However, such an arrangement is not required in all embodiments. In some embodiments, the teeth 72 may be spaced apart some amount, so that a significant space 78 exists between the bases 76 of adjacent teeth 72. See FIG. 11. When a pawl 102a,102b of spring member 100 is disposed in this space 78, the bone plates 40,80 may move relative to each other, both forward and backward, some small limited amount. With such an arrangement, small movements by the patient that might otherwise cause the bone plate device 30 to ratchet to the next shorter increment are allowed without causing such ratcheting. Such spaces 78 may be limited to being not more the size of the base 76 of the teeth 72, so that, in effect, the toothed section 70a,70b has the appearance of every other tooth 72 being removed. Other tooth profiles and tooth/teeth configurations are also possible, such staggering teeth 72 on the different toothed sections 70a,70b, curved profiles for the teeth 72, and the like.

Figure 12:
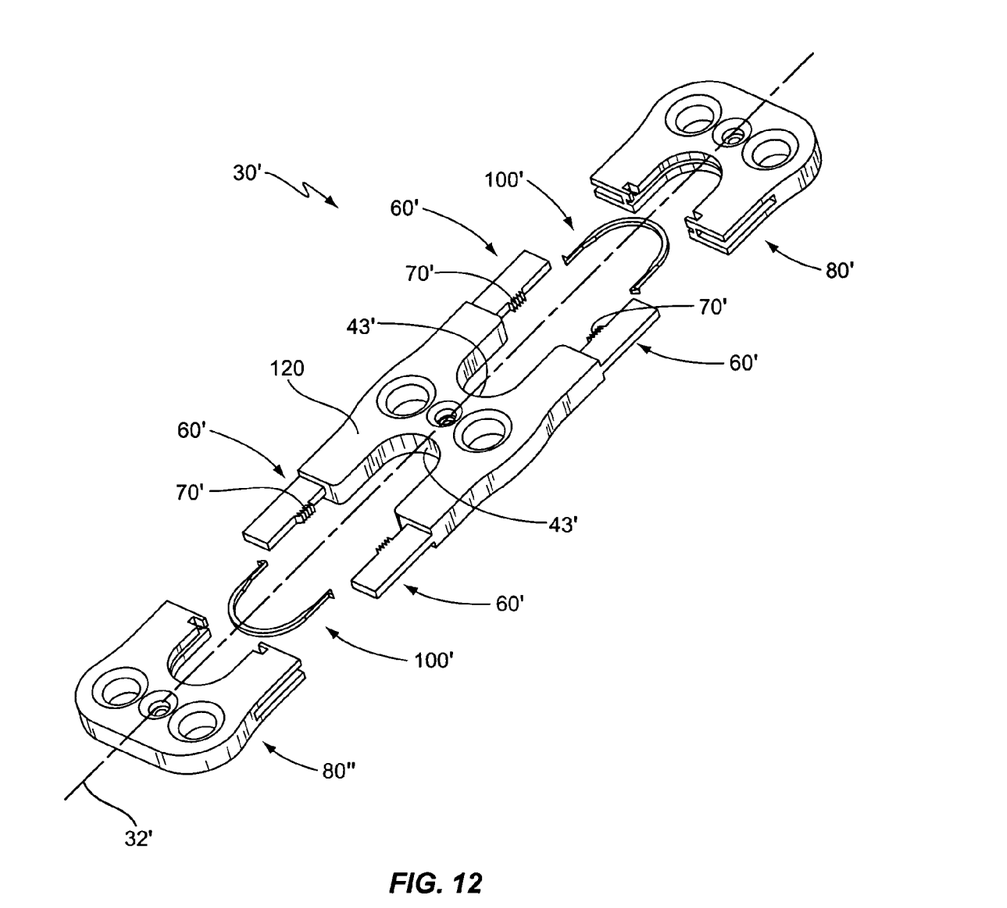
FIG. 12 shows an exploded view of one multi-level embodiment of the bone plate device.
Figure 13:
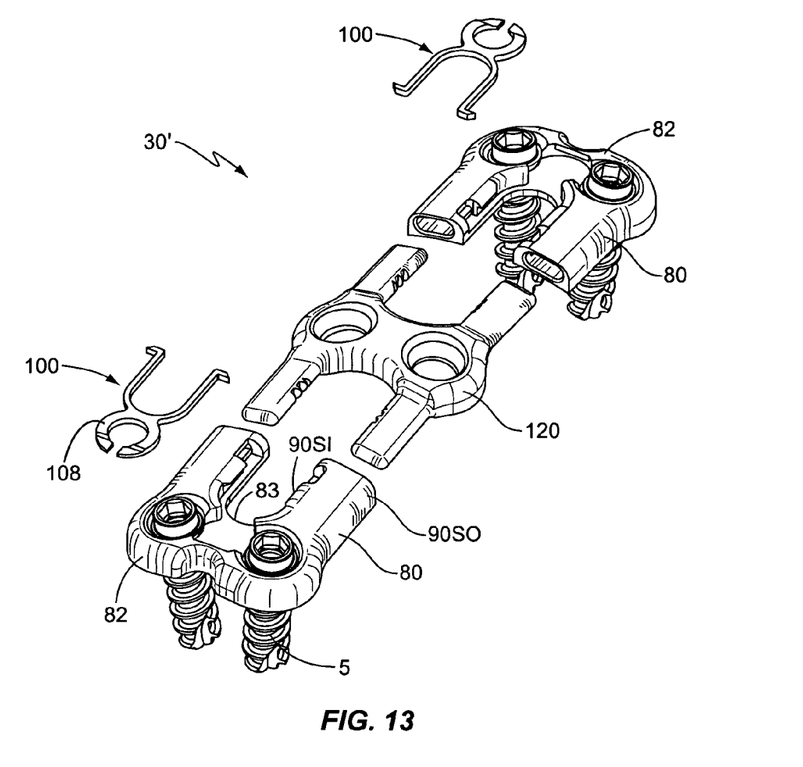
FIG. 13 shows an exploded view of another multi-level embodiment of the bone plate device.
Figure 14:
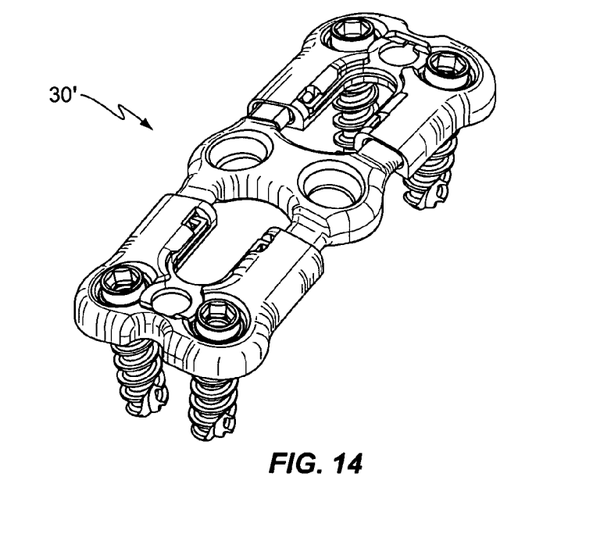
FIG. 14 shows the device of FIG. 13 in an assembled state.
Figure 15:
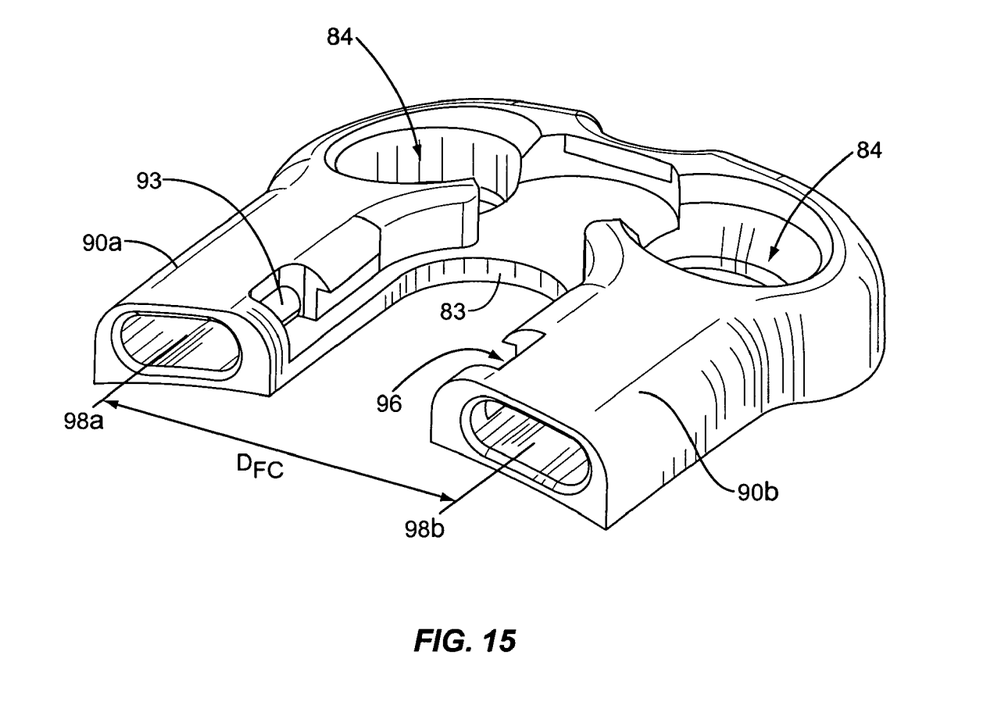
FIG. 15 shows one embodiment of a "female" bone plate portion suitable for use in the bone plate device embodiment of FIG. 13.

The discussion above has been in terms of a bone plate device 30 having two bone plates 40,80 for fixing two adjacent vertebrae V1,V2. However, some embodiments of the bone plate device 30 may have more bone plates for fixing together more than two vertebrae. For example, the multi-level bone plate device 30' of FIGS. 12-14 has three bone plates for fixing three adjacent vertebrae V1,V2,V3. Two of the bone plates, the upper and lower bone plates 80',80", may be as described above for bone plate 80. The other bone plate, the center bone plate 120, may be somewhat similar to bone plate 40 described above, but with four arms 60', two on each end. Thus, the center bone plate 120 of such an embodiment has four arms 60' with four corresponding toothed sections 70', and two curved sections 43'. For such a bone plate 120, the terms "proximal" and "distal" are with reference to the midline thereof perpendicular to the longitudinal axis 32' of the overall bone plate device 30'. In addition, such a device 30' may have two spring members 100' similar to spring member 100 discussed above. For such a configuration, the upper and lower bone plates 80',80" move toward the center bone plate 120 from generally opposite directions along the longitudinal axis 32' of the bone plate device 30'. To use such a multi-level device, the upper bone plate 80' is secured to an upper vertebrae V1, the center bone plate 120 is secured to a middle vertebrae V3, and the lower bone plate 80" is secured to a lower vertebrae V2. The installation and movement limiting action of such a device 30' is substantially as described above.

Figure 16:
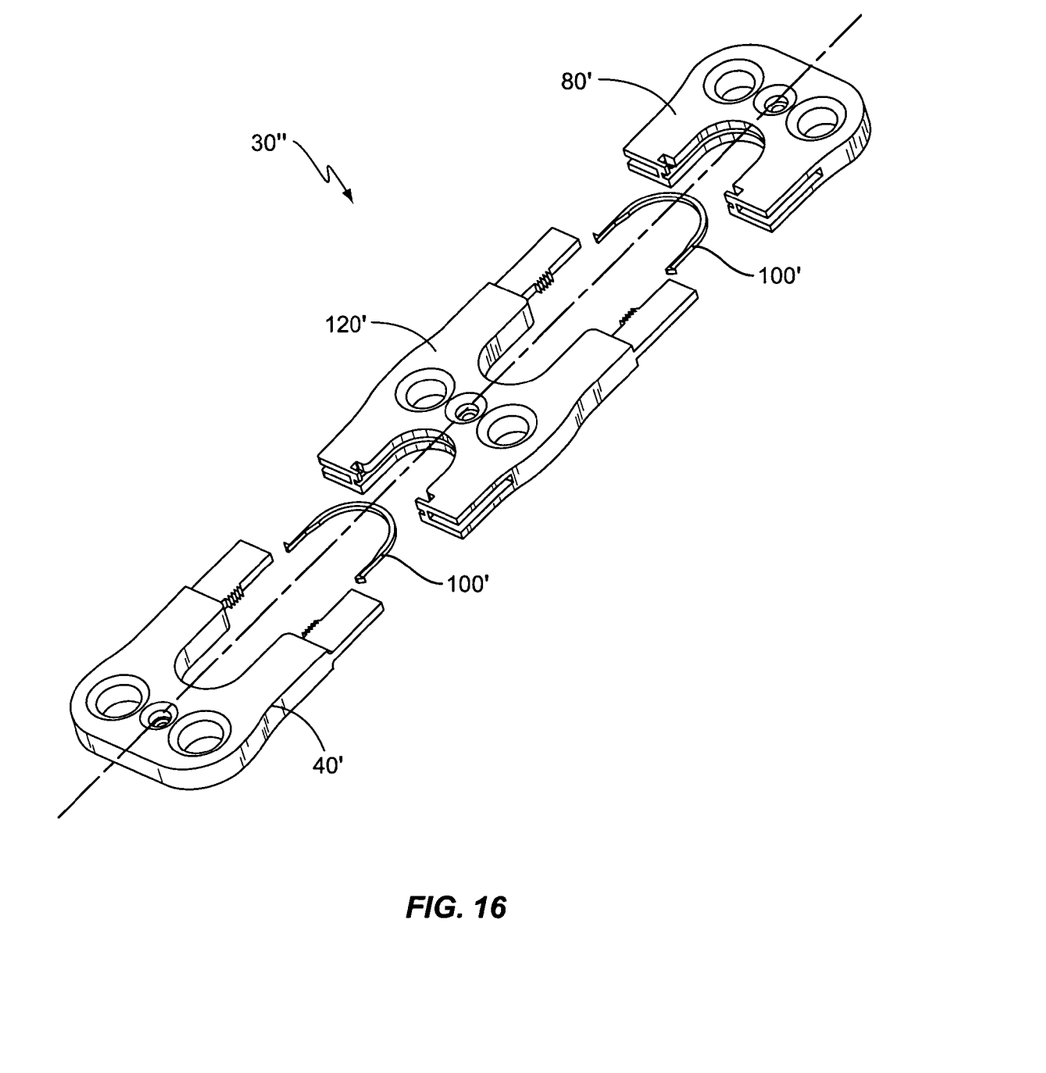
FIG. 16 shows an exploded view of yet another multi-level embodiment of the bone plate device, displaying one approach to reversing the male/female relationship with respect to the embodiment of FIG. 12.

It should be understood that the male/female relationship of the embodiments discussed above may be reversed without departing from the scope of the present invention. For example, another embodiment of a multi-level bone plate device is shown in FIG. 16. This multi-level embodiment of the bone plate device 30" is similar to that described immediately above, but with the male/female relationship reversed for the connection between center bone plate 120' and lower bone plate 40'. Thus, the center bone plate 120', has two male arms (like arms 60a,60b) extending toward upper bone plate 80', and two female arm (like arms 90a,90b) extending toward lower bone plate 40'.

The bone plates 40,40',80,80',80", and spring members 100,100' may be made from any material or materials, such as titanium, poly-ether-ether-ketone (PEEK), or the like, compatible for use in an animal body over significant periods of time. Bioabsorbable and/or resorbable materials may alternatively used.

The various embodiments of the bone plate device 30,30', 30" may be used in various locations in the animal body, including without limitation anterior or lateral locations on the cervical, thoracic, and lumbar portions of the spinal column.

Other embodiments of the present invention may be carried out in other specific ways than those herein set forth without departing from the scope and essential characteristics of the invention. The terms "upper", "lower", "inner", "outer", and the like are terms to describe the relative positioning of different elements, and are used in a general sense. The present embodiments are, therefore, to be considered in all respects as illustrative and not restrictive, and all changes coming within the meaning and equivalency range of the appended claims are intended to be embraced therein.

What is claimed is:

1. A bone plate device comprising:
   a first plate member adapted to be secured to a bone;
   a second plate member adapted to be secured to a bone and coupled to said first plate member;
   said first plate member including a first base section and first and second arms spaced from one another and extending from the first base section towards the second plate, the first base section and the first and second arms defining a first gap;
   said second plate member including a second base section and third and fourth arms spaced apart from one another and extending from the second base section toward said first plate member, said third arm engaging said first arm and said fourth arm engaging said second arm, the second base section and the third and fourth arms defining a second gap;
   said first plate member having first and second toothed sections thereon disposed on opposite sides of a longitudinal axis of said bone plate device, each of said toothed sections comprising a plurality of teeth;
   a spring member engaging said second plate member and displaceably engaging said first and second toothed sections;
   a groove extending along said third arm, across said second base section, and along said fourth arm; wherein said spring member is disposed in said groove;
   wherein engagement of said spring member and said toothed sections enables progressive sliding advancement of said plate members toward one another and limits movement of said plate members away from one another;
   the first and second gaps together form a single visualization port that is adjustable in size depending upon an amount of the sliding advancement of said plate members.

2. The device of claim 1 wherein said spring member comprises a generally U-shaped spring member abutting said first and second plate members and distinct therefrom.

3. The device of claim 2 wherein said spring member comprises first and second integral pawls for displaceable engagement said first and second toothed sections, respectively.

4. The device of claim 3 wherein said first and second pawls point in generally opposite directions and wherein said first and second pawls are disposed on opposite sides of said axis of said bone plate device.

5. The device of claim 1 wherein said first and second arms include said first and second toothed sections thereon, respectively.

6. The device of claim 1 wherein said first plate member comprises a first curved section; wherein said second plate member comprises a second curved section;
   wherein said first and second curved sections define outer ends of the visualization port through said bone device when said first and second plates are disposed a maximum amount toward one another, said visualization port having a width in a direction generally transverse to a line connecting said first and second curved surfaces that is approximately equal to a distance between said first and second toothed sections.

7. The device of claim 1 further comprising at least a first fastener securing said second plate member to the bone; wherein said spring member restrains said first fastener against backing out after said fastener is fully installed.

8. The device of claim 7 further comprising at least a second fastener securing said second plate member to the bone; wherein said spring member further restrains both said first and second fasteners against backing out after said fasteners are fully installed.

9. The device of claim 1 where said toothed sections comprise a plurality of teeth having bases and a plurality of spaces between the bases of said teeth.

10. The device of claim 1 further comprising:
    a third plate member adapted to be secured to a bone and engaging at least one of said first and second plate members;
    third and fourth toothed sections spaced from one another and each comprising a plurality of teeth;
    a second spring member displaceably engaging said third and fourth toothed sections;
    wherein engagement of said second spring member and said third and fourth toothed sections enables progressive sliding advancement of said third plate member toward said one plate member and limits movement of said third plate member away from said one plate member.

11. The device of claim 10 wherein said third plate member is disposed closer to said first plate member than said second plate member.

12. The device of claim 1:
    wherein said first and second arms are disposed on opposing sides of said axis; each of said first and second arms having an associated centerline;
    wherein said first and second toothed sections are disposed on inner surfaces, with respect to said axis, of said first and second arms, respectively;
    wherein said third arm extends farther inward toward said axis than said first arm and extends farther outward away from said axis than said centerline of said first arm.

13. The device of claim 1 wherein distal portions of said first arm are substantially enclosed by said third arm.

14. The device of claim 1:
    further including said first and second arms having said first and second toothed sections thereon, respectively;
    said first and second arms spaced from one another and disposed on opposing sides of said axis;
    first and second centerlines associated with said first and second arms, respectively, and spaced from each other a first distance;
    including said third and fourth arms extending toward said first plate member and disposed on opposing sides of said longitudinal axis;

third and fourth centerlines associated with said third and fourth arms, respectively, and spaced from each other a second distance;

wherein said first and second distances are approximately equal.

15. The device of claim 1:

wherein said spring member comprises a generally U-shaped spring member abutting said first and second plate members and distinct therefrom; said spring member comprising first and second integral pawls for displaceable engagement said first and second toothed sections, respectively;

wherein said first and second arms are spaced from one another and disposed on opposing sides of said axis; wherein said first and second toothed sections are disposed on inner surfaces, with respect to said axis, of said first and second arms, respectively;

first and second centerlines associated with said first and second arms, respectively, and spaced from each other a first distance;

wherein said second plate member has the second base section extending between said third and fourth arms, and a groove extending along said third arm, across said second base section, and along said fourth arm; wherein said spring member is disposed in said groove; said third arm engaging said first arm and said fourth arm engaging said second arm;

third and fourth centerlines associated with said third and fourth arms, respectively, and spaced from each other a second distance; wherein said first and second distances are approximately equal;

wherein said third arm extends farther inward toward said axis than said first arm and extends farther outward away from said axis than said centerline of said first arm;

wherein distal portions of said first arm are substantially enclosed by said third arm;

further comprising at least a first fastener securing said second plate member to the bone; wherein said spring member restrains said first fastener against backing out after said fastener is fully installed.

16. The device of claim 15 further comprising:

a third plate member adapted to be secured to a bone and coupled to said second member;

third and fourth toothed sections spaced from one another and each comprising a plurality of teeth;

a second spring member displaceably engaging said third and fourth toothed sections;

wherein engagement of said second spring member and said third and fourth toothed sections enables progressive sliding advancement of said second and third plates toward one another and limits movement of said second and third plates away from one another.

17. A bone plate device comprising:

a first plate member adapted to be secured to a bone and having first and second arms spaced from one another and disposed on opposing sides of a longitudinal axis of said bone plate device; each of said first and second arms having an associated centerline; each said first and second arms having an inner surface, with respect to said axis, having first and second toothed sections thereon respectively, each of said toothed sections comprising a plurality of teeth;

a second plate member adapted to be secured to a bone and coupled to said first plate member; said second plate member having third and fourth arms spaced from one another with a gap there between, the third and fourth arms extending toward said first plate member; said third arm engaging said first arm and said fourth arm engaging said second arm;

a generally U-shaped spring member abutting said first and second plate members and distinct therefrom, said spring member displaceably engaging said second plate member and said first and second toothed sections;

wherein said third arm extends inward toward said axis farther than said first arm and extends farther outward away from said axis than said centerline of said first arm;

wherein said toothed sections form a portion of a locking mechanism that allows progressive sliding advancement of said plate members toward one another and limits movement of said plate members away from one another.

18. The device of claim 17 wherein said third arm extends at least as far out from said axis as said first arm.

19. The device of claim 18 wherein distal portions of said first arm are substantially enclosed by said third arm.

20. The device of claim 17 wherein said third arm has top, bottom, outer, and inner surfaces circumferentially enclosing a distal portion of said first arm.

21. The device of claim 20:

wherein said fourth arm extends inward toward said axis farther than said second arm and extends farther outward away from said axis than said centerline of said second arm;

wherein said fourth arm has top, bottom, outer, and inner surfaces circumferentially enclosing a distal portion of said second arm.

22. The device of claim 17 wherein said second plate member has a base section extending between said third and fourth arms; and further comprising a groove extending along said third arm, across said base section, and along said fourth arm; wherein said spring member is disposed in said groove.

23. The device of claim 17 further comprising at least a first fastener securing said second plate member to the bone; wherein said spring member restrains said first fastener against backing out after said fastener is fully installed.

24. The device of claim 23 further comprising at least a second fastener securing said second plate member to the bone; wherein said spring member further restrains both said first and second fasteners against backing out after said fasteners are fully installed.

25. The device of claim 17 where said toothed sections comprise a plurality of teeth having bases and a plurality of spaces between the bases of said teeth.

26. The device of claim 17:

further comprising a third plate member adapted to be secured to a bone and engaging one of said first and second plate members; said third plate member having fifth and sixth arms spaced from one another and disposed on opposing sides of said axis of said bone plate device; each of said fifth and sixth arms having an associated centerline;

wherein said one plate member further comprises seventh and eighth arms extending away from said one plate member; said seventh arm engaging said fifth arm and said eighth arm engaging said sixth arm;

further comprising third and fourth toothed sections forming a portion of a second locking mechanism that allows progressive sliding advancement of said third plate member toward said one plate member and limits movement of said third plate member and said one plate member away from one another.

27. The device of claim 26 wherein said third and fourth toothed sections are disposed on said seventh and eighth arms, respectively.

28. The device of claim 26 wherein said one plate member is said second plate member.

29. The device of claim 26 wherein said one plate member is said first plate member.

30. The device of claim 26 wherein said third and fourth toothed sections are disposed on said fifth and sixth arms, respectively.

31. The device of claim 17:
wherein said third arm has top, bottom, outer, and inner surfaces circumferentially enclosing a distal portion of said first arm;
wherein said fourth arm extends inward toward said axis farther than said second arm and extends farther outward away from said axis than said centerline of said second arm;
wherein said fourth arm has top, bottom, outer, and inner surfaces circumferentially enclosing a distal portion of said second arm;
further comprising a generally U-shaped spring member abutting said first and second plate members and distinct therefrom, said spring member displaceably engaging said second plate member and said first and second toothed sections; wherein said spring member comprises first and second integral pawls for displaceable engagement said first and second toothed sections, respectively;
wherein said second plate member has a base section extending between said third and fourth arms; and further comprising a groove extending along said third arm, across said base section, and along said fourth arm; wherein said spring member is disposed in said groove;
further comprising at least a first fastener securing said second plate member to the bone; wherein said spring member restrains said first fastener against backing out after said fastener is fully installed.

32. The device of claim 31:
further comprising a third plate member adapted to be secured to a bone and engaging one of said first and second plate members; said third plate member having fifth and sixth arms spaced from one another and disposed on opposing sides of said axis of said bone plate device; each of said fifth and sixth arms having an associated centerline;
wherein said one plate member further comprises seventh and eighth arms extending away from said one plate member; said seventh arm engaging said fifth arm and said eighth arm engaging said sixth arm;
further comprising third and fourth toothed sections forming a portion of a second locking mechanism that allows progressive sliding advancement of said third plate member toward said one plate member and limits movement of said third plate member and said one plate member away from one another.

33. A method of fixing two vertebrae together using a bone plate device having at least two bone plate members, comprising:
securing a first plate member to a first vertebrae by inserting a first fastener through an opening in the first plate member and into the vertebrae; said first plate member having first and second arms with toothed sections thereon disposed on opposite sides of a longitudinal axis of said bone plate device, each of said toothed sections comprising a plurality of teeth;
securing a second plate member adapted to a second vertebrae by inserting a second fastener through an opening in the second plate member and into the vertebrae, wherein said second plate member has third and fourth arms, a base section extending therebetween, and a groove extending along said third arm, across said base section, and along said fourth arm;
coupling said second plate member with said first plate member so as to enable progressive sliding advancement of said plate members toward one another and limit movement of said plate members away from one another by displaceably engaging a spring member with said first and second toothed sections while said spring member engages said second plate member, wherein said spring member engaging said second plate member comprises said spring member being disposed in said groove; and
progressively sliding the plate members towards one another and reducing a size of a visualization port formed by intersecting gaps between the opposing arms of each of the first and second plate members.

34. The method of claim 33 wherein displaceably engaging said spring member with said first and second toothed sections comprises deflecting distal portions of a generally U-shaped spring member that is distinct from said first and second plate members.

35. The device of claim 34 wherein said spring member comprises first and second integral pawls; and wherein displaceably engaging said spring member with said first and second toothed sections comprises displaceably engaging first and second pawls of said spring member with said first and second toothed sections, respectively.

36. The method of claim 33 including restraining said first fastener against backing out by said spring member.

37. The method of claim 33 wherein coupling said second plate member with said first plate member so as to limit movement of said plate members away from one another comprises disposing pawl sections of said spring member in spaces disposed between the bases of the teeth of said toothed sections.

38. The method of claim 33 further comprising:
securing a third plate member to a third vertebrae;
engaging said third plate member with one of said first and second plate members so as to enable progressive sliding advancement of said third plate member toward said one plate member and limit movement of said third plate member away from said one plate member by displaceably engaging a second spring member associated with either said third plate member or said one plate member with third and fourth toothed sections associated with the other of said third plate member and said one plate member.

39. The method of claim 38 wherein said one plate member is said first plate member.

40. The method of claim 38 wherein said one plate member is said second plate member.

41. A method of fixing two vertebrae together using a bone plate device having at least two bone plate members, comprising:
securing a first plate member to a first vertebra; said first plate member having first and second arms extending outward from the first plate member and disposed on opposite sides of a longitudinal axis of said bone plate device with a first gap there between; each of said first and second arms having an associated centerline; each said first and second arms having an inner surface, with respect to said axis, having first and second toothed sections thereon respectively, each of said toothed sections comprising a plurality of teeth;

securing a second plate member adapted to a second vertebra; said second plate member having third and fourth arms extending outward from the second plate member and toward said first plate member with a second gap there between;

engaging said first arm with said third arm such that said third arm extends inward toward said axis farther than said first arm and extends outward away from said axis farther than said centerline of said first arm;

engaging said second arm with said fourth arm;

coupling said second plate member with said first plate member so as to enable progressive sliding advancement of said plate members toward one another and limit movement of said plate members away from one another via said toothed sections; and attaching the first and second plate members to the first and second vertebrae, respectively, and forming a window by adjoining the first and second gaps;

wherein said second plate member has a base section extending between said third and fourth arms; and further comprising disposing a spring member in a groove extending along said third arm, across said base section, and along said fourth arm; and further comprising thereafter engaging said toothed sections with said spring member so as limit movement of said first and second plate members away from one another.

42. The method of claim 41 wherein coupling said second plate member with said first plate member comprises deflecting distal portions of a generally U-shaped spring member that is distinct from said first and second plate members to engage said toothed sections.

43. The method of claim 41 wherein engaging said first arm with said third arm such that said third arm extends inward toward said axis farther than said first arm and extends farther outward away from said axis than said centerline of said first arm comprises engaging said first arm with said third arm such that said third arm extends inward toward said axis farther than said first arm and extends outward away from said axis farther said first arm where the two overlap.

44. The method of claim 41 wherein engaging said first arm with said third arm comprises substantially circumferentially enclosing a distal portion of said first arm with said third arm.

45. The method of claim 41:

wherein engaging said first arm with said third arm comprises substantially circumferentially enclosing a distal portion of said first arm with said third arm; and wherein engaging said second arm with said fourth arm comprises substantially circumferentially enclosing a distal portion of said second arm with said fourth arm.

46. The method of claim 41 wherein securing said second plate member to the second vertebrae comprises securing said second plate member to the second vertebrae using at least a first fastener, and further comprising thereafter restraining said first fastener against backing out by said spring member.

47. The method of claim 46 wherein securing said second plate member to the second vertebrae comprises securing said second plate member to the second vertebrae using at least first and second fasteners, and further comprising thereafter restraining said first and second fasteners against backing out by said spring member.

48. The method of claim 41 wherein coupling said second plate member with said first plate member comprises disposing pawl sections of a spring member in spaces disposed between the bases of the teeth of said toothed sections.

49. The method of claim 41 further comprising:

securing a third plate member to a third vertebrae; said third plate member having fifth and sixth arms disposed on opposite sides of said longitudinal axis; each of said fifth and sixth arms having an associated centerline;

engaging said fifth arm with a seventh arm and engaging said sixth arm with an eighth arm, said seventh and eighth arms associated with one of said first and second plate members, so as to enable progressive sliding advancement of said third plate member toward said one plate member and limit movement of said third plate member away from said one plate member another via said third and fourth toothed sections, said third and fourth toothed sections comprising a plurality of teeth.

50. The method of claim 49 wherein said one plate member is said second plate member.

51. The method of claim 50 wherein said second plate member comprises said third and fourth toothed sections.

* * * * *